(12) United States Patent
Song et al.

(10) Patent No.: US 11,454,114 B2
(45) Date of Patent: Sep. 27, 2022

(54) METHOD FOR CONSTRUCTING GROUNDWATER MONITORING WELL INSIDE PRB TRENCH

(71) Applicant: INSTITUTE OF SOIL SCIENCE, CHINESE ACADEMY OF SCIENCES, Suzhou (CN)

(72) Inventors: Xin Song, Jiangsu (CN); Peng Jin, Jiangsu (CN); Changlong Wei, Jiangsu (CN); Kang Li, Jiangsu (CN); Zhiwen Tang, Jiangsu (CN); Heng Fu, Jiangsu (CN); Xing Chen, Jiangsu (CN)

(73) Assignee: INSTITUTE OF SOIL SCIENCE, CHINESE ACADEMY OF SCIENCES, Jiangsu (CN)

( * ) Notice: Subject to any disclaimer, the term of this patent is extended or adjusted under 35 U.S.C. 154(b) by 0 days.

(21) Appl. No.: 17/568,726

(22) Filed: Jan. 5, 2022

(65) Prior Publication Data
US 2022/0127960 A1 Apr. 28, 2022

Related U.S. Application Data

(63) Continuation of application No. PCT/CN2020/088955, filed on May 7, 2020.

(30) Foreign Application Priority Data

Jul. 5, 2019 (CN) .......................... 201910604853.9

(51) Int. Cl.
*E21B 49/08* (2006.01)
*C02F 1/00* (2006.01)
(Continued)

(52) U.S. Cl.
CPC .......... *E21B 49/0875* (2020.05); *C02F 1/004* (2013.01); *E02D 17/08* (2013.01);
(Continued)

(58) Field of Classification Search
CPC ...... E21B 49/0875; E21B 7/205; E21B 19/00; C02F 1/004; C02F 2101/22;
(Continued)

(56) References Cited

U.S. PATENT DOCUMENTS

| | | | |
|---|---|---|---|
| 2003/0035691 A1* | 2/2003 | Sivavec | ................ B09C 1/002 210/170.07 |
| 2018/0229281 A1* | 8/2018 | Alexander | ............... B09C 1/06 |

(Continued)

FOREIGN PATENT DOCUMENTS

| | | |
|---|---|---|
| CN | 104973632 | 10/2015 |
| CN | 105668680 | 6/2016 |

(Continued)

OTHER PUBLICATIONS

"International Search Report (Form PCT/ISA/210) of PCTICN2020/088955," dated Aug. 12, 2020, with English translation thereof, pp. 1-4.

(Continued)

*Primary Examiner* — Fred Prince
(74) *Attorney, Agent, or Firm* — JCIP Global Inc.

(57) ABSTRACT

Disclosed is a method for installing a groundwater monitoring well inside a permeable reactive barrier (PRB) trench including excavating a PRB trench, installing a trench side-wall support, positioning a monitoring well borehole, installing an outer installation casing for pre-burying the monitoring well, installing a monitoring well positioning bracket, installing a monitoring well casing, installing monitoring well filter packs and seal materials, filling the trench with PRB media and capping with a covering soil layer, removing the outer installation casing, removing the trench side-wall support, completing the monitoring well with a wellhead, and conducting well development. This method avoids the complex procedure of re-drilling a borehole (Continued)

within the PRB media following the completion of PRB construction and media filling, assures that monitoring well installation protocols are followed and high quality and stable operation is achieved, and serves for groundwater monitoring to support the implementation and efficacy evaluation of the PRB technology.

8 Claims, 4 Drawing Sheets

(51) Int. Cl.
| | | |
|---|---|---|
| E02D 17/08 | (2006.01) | |
| E02F 5/08 | (2006.01) | |
| E02F 5/10 | (2006.01) | |
| E21B 19/00 | (2006.01) | |
| G01N 33/18 | (2006.01) | |
| B09C 1/00 | (2006.01) | |
| E21B 7/20 | (2006.01) | |
| C02F 101/22 | (2006.01) | |
| C02F 103/06 | (2006.01) | |

(52) U.S. Cl.
CPC .................. *E02F 5/08* (2013.01); *E02F 5/10* (2013.01); *E21B 7/205* (2013.01); *E21B 19/00* (2013.01); *G01N 33/18* (2013.01); *B09C 1/002* (2013.01); *C02F 2101/22* (2013.01); *C02F 2103/06* (2013.01); *C02F 2201/004* (2013.01)

(58) Field of Classification Search
CPC ........... C02F 2103/06; C02F 2201/004; E02D 17/08; E02F 5/08; E02F 5/10; G01N 33/18; B09C 1/002
USPC .......................... 210/747.7, 170.07; 166/276
See application file for complete search history.

(56) References Cited

U.S. PATENT DOCUMENTS

2019/0329306 A1\* 10/2019 Major ........................ F23G 7/14
2019/0366401 A1\* 12/2019 Swearingen ............ B09C 1/002

FOREIGN PATENT DOCUMENTS

| CN | 105954464 | 9/2016 |
|---|---|---|
| CN | 110409405 | 11/2019 |
| KR | 100838426 | 6/2008 |

OTHER PUBLICATIONS

"Written Opinion of the International Searching Authority (Form PCT/ISA/237) of PCT/CN2020/088955," dated Aug. 12, 2020, with English translation thereof, pp. 1-12.

\* cited by examiner

METHOD FOR CONSTRUCTING GROUNDWATER MONITORING WELL INSIDE PRB TRENCH

CROSS-REFERENCE TO RELATED APPLICATIONS

The presented application is a continuation of international PCT application serial No. PCT/CN2020/088955 filed on May 7, 2020, which claims the priority of the Chinese Patent Application No. 201910604853.9, filed on Jul. 5, 2019 and entitled "METHOD FOR CONSTRUCTING GROUNDWATER MONITORING WELL INSIDE PRB TRENCH". The entirety of each of the above mentioned patent applications is hereby incorporated by reference herein and made a part of this specification.

TECHNICAL FIELD

The presented invention relates to the field of soil and groundwater remediation technologies, and in particular, to a method for constructing a groundwater monitoring well inside a permeable reactive barrier (PRB) trench.

RELATED ART

In recent years, with the continuous acceleration of China's urbanization process, heavy metals, organic compounds, inorganic anions, radioactive substances, etc. that were generated during manufacture and daily lives enter the groundwater system through a variety of pathways, resulting in serious contamination to the groundwater, and causing widespread concern from all stakeholders and governments at all levels. Therefore, implementation of groundwater remediation is one of the important tasks in pollution prevention and control for ecological environment in China. Over the past 30 years, researchers have done a great deal of work on sustainable groundwater remediation technologies, among which in-situ remediation becomes a center of focus. The in-situ remediation technology has advantages such as relatively low treatment costs, less aboveground disturbances, and less chances of exposure to the contaminants. As an in-situ remediation technology, PRB is characterized by low construction costs, no need for external power, high treatment effectiveness, low operating costs, sustainable in-situ remediation, and low interference with the ecological environment.

Introduced by the United States Environmental Protection Agency (USEPA) in 1980s, PRB is usually installed downstream of a groundwater contaminant plume, and constructed by filling a mixture of reactive media and inert support materials in an underground trench that is perpendicular to the direction of groundwater flow, and has higher permeability compared to the surrounding geological soil layers, thus creating an in-situ remediation system. When contaminated groundwater flows through the PRB, the organics, heavy metals, radioactive substances, and other contaminants that are dissolved in groundwater undergo biological, chemical or physical reactions with the reactive media to promote degradation, precipitation, adsorption, and interception, and thus removed from groundwater as the remedial objectives for the contaminated groundwater is achieved. At present, most of the PRB related research in China is still at the stage of fundamental studies in laboratories, mainly focusing on the selection and optimization of PRB filling media, column experiments, simulation of removal process, etc. According to available information, four PRB projects have been implemented up to date.

The evaluation of effectiveness of PRB technologies implemented in contaminated groundwater remediation is typically performed via installing monitoring wells located upstream, downstream, and inside a PRB trench and conducting groundwater sampling and analysis. China's PRB technology is still in the early stage of development. Compared with installation of monitoring wells located upstream and downstream of a PRB, installation method of groundwater monitoring wells inside a PRB trench is not well developed yet. Currently, installation of monitoring wells inside a PRB trench is primarily completed via two methods. The first method involves drilling in a PRB trench after the trench has been filled with media. This method has disadvantages such as need for redundant construction work, disturbance of trench media permeability, damage to trench structure, loss of reactive media, impact on PRB lifespan, and increase in construction costs. On the other hand, the second method involves concurrent actions of trench filling with media and pre-burying of monitoring well screens and casings when a PRB is constructed. This method does not adopt proper fixing devices, has problems such as extensive construction and low personnel safety, and further easily causes clog of monitoring wells and damage to well materials since filter packs are not placed around well screens. According to the "Technical Guidelines for the Construction of Groundwater Environmental Monitoring Wells (draft for comments)" issued by the China National Environmental Monitoring Center in 2013, and the "Specifications for the Construction of Groundwater Monitoring Wells" issued by the Ministry of Land and Resources of the People's Republic of China in 2014, the quality of well completion using these methods does not meet the requirements for long-term and accurate understanding of groundwater quality and dynamic distribution and transformation of contaminants in groundwater. A standardized and efficient well construction method may not only improve the quality of groundwater monitoring wells inside the PRB trench, but also provide assurances for obtaining feasible and reliable long-term PRB operating performance and maintenance data, and thus play an important role for ensuring long-term safe operation of PRB and reducing adverse impacts of contaminated sites on ecological environment.

SUMMARY OF INVENTION

The technical problem to be solved is as follows: In view of the above-mentioned problems of existing monitoring well construction methods inside PRB trenches, such as redundant constructions, disturbance of the permeability of trench media, damage to trench structure, loss of reactive media, impact on PRB lifespan, increase in construction costs, extensive construction, and low personnel safety, this presented invention provides a scientific, reliable, safe and standardized method for constructing a groundwater monitoring well inside a PRB trench, which may improve the quality of monitoring wells, avoid redundant construction, reduce scope of engineering work and disturbance to PRB trench, easy to implement, and comply with well construction specifications, thereby provide technical assurances for obtaining scientific and reliable PRB operating parameters and data.

The presented invention adopts the following technical solutions:

Step 1: Excavating a PRB trench: Excavate with trenching equipment for the construction of a PRB trench, to the design depth, width and length, and clearing soil from the excavated trench;

Step 2: Installing a trench side-wall support: When a rotary drilling machine is used to excavate the PRB trench, a large-diameter steel casing serves as the trench side-wall support; when a long-reach excavator or a double-wheel milling machine is used to excavate the PRB trench, steel sheet piles serve as the trench side-wall support; Step 3: Positioning a monitoring well borehole: Determine the installation location of a groundwater monitoring well inside the trench at the center of a large-diameter steel casing or at a location between the mid-point between the steel sheet piles on both sides of the trench side-wall, and drill 0.3 to 0.5 meters into the aquiclude layer at the bottom of the trench with a drilling machine to form the monitoring well borehole, and use this borehole as the positioning and fixing support point for the bottom of the monitoring well pipe;

Step 4: Installing an outer installation casing for pre-burying the monitoring well: Place, with a crane or vibratory hammer, the outer installation casing for pre-burying the monitoring well at the bottom of the excavated PRB trench, wherein the outer installation casing is coaxial with the monitoring well borehole mentioned above in Step 3;

Step 5: Installing a monitoring well positioning bracket: The rebar monitoring well positioning bracket includes a hoop mounted outside the outer installation casing for pre-burying the monitoring well and a retaining structure attached to the hoop, wherein the hoop is formed into a ring shape by rolling and pressing a steel bar; the retaining structure is a set of straight rebars with one end welded to the hoop and the other end extended to the trench side-wall support;

Step 6: Installing the monitoring well pipe: The monitoring well pipe consists of a PVC well casing (unslotted pipe), a well screen (slotted pipe), and a sand-settling casing (unslotted pipe) at the bottom, which is assembled with the well casing connected to the top of the well screen and the sand-settling casing connected to the bottom of the well screen; following the completion of assembly, lower the assembled monitoring well pipe into the outer installation casing for pre-burying the monitoring well using a crane and place the bottom of the monitoring well pipe into the fixing support point (previously drilled monitoring well borehole mentioned above in Step 3);

Step 7: Installing monitoring well filter packs and seal materials: Fill the space between the monitoring well pipe and the outer installation casing for pre-burying the monitoring well with the filter packs; then fill the space with buffering sands on the top of the filter packs to a thickness of 0.5 to 1 meter; and at last fill the space with bentonite from the top of buffering sands to ground surface to seal the outer installation casing for pre-burying the monitoring well;

Step 8: Backfilling the trench with PRB media: Backfill the trench with PRB media between the trench side-wall support and the outer installation casing for pre-burying the monitoring well, in layers of a thickness of 2 meters, wherein the trench backfill materials include PRB media and a covering soil layer;

Step 9: Removing the outer installation casing for pre-burying the monitoring well: Suspend backfilling every time the thickness of backfilled media reaches 2 meters, pull up the outer installation casing for pre-burying the monitoring well with a crane or vibratory hammer by 2 meters, and resume backfilling afterwards; repeat the alternated operations of backfilling PRB media and pulling up the outer installation casing for pre-burying the monitoring well until the PRB trench is completely backfilled and the outer installation casing for pre-burying the monitoring well is completely pulled out of the ground; in this way, installation of the monitoring well and backfilling the PRB trench are completed concurrently;

Step 10: Removing the trench side-wall support: Following removal of the outer installation casing for pre-burying the monitoring well, remove the trench side-wall support with a vibratory hammer or a hoisting device; and Step 11: Conducting well completion and well development: Lastly, install a well head assembly for the groundwater monitoring well installed inside the PRB trench, and conduct well development for the installed groundwater monitoring well to complete preparation for groundwater sampling.

In an embodiment, the design depth of the PRB trench in Step 1 is 0.5 to 1 meter into the aquiclude layer; the aquiclude layer is a bedrock or clay layer; the design width of the PRB trench is 1 to 3 meters; and the trenching equipment is a rotary drilling machine, a turntable drilling machine, a long-reach excavator or a double-wheel milling machine.

In an embodiment, the large-diameter steel casing in Step 2 has a diameter larger than 1 meter, and the steel sheet piles are to be installed as forced into ground by vibration of a vibratory hammer on both sides of the PRB trench.

In an embodiment, the size of the drill bit in Step 3 is determined by the design diameter of the monitoring well pipe and the diameter of the monitoring well pipe ranges from 50 millimeters to 160 millimeters.

In an embodiment, the material of outer installation casing for pre-burying the monitoring well in Step 4 is steel, and the diameter of the monitoring well is larger than or equal to 110 millimeters; the inner diameter of the outer installation casing for pre-burying the monitoring well is larger than the outer diameter of the monitoring well pipe by at least 10 centimeters, and the length of the outer installation casing for pre-burying the monitoring well is 0.3 to 0.5 meters longer than the design depth of the PRB trench.

In an embodiment, the material of the monitoring well positioning bracket in Step 5 is steel, and the hoop has an inner diameter of 2 to 4 millimeters greater than the outer diameter of the outer installation casing for pre-burying the monitoring well; the retaining structure is made of rebar; when a large-diameter steel casing is used as the trench side-wall support, the retaining structure is fabricated with three legs with equal angles, which extend to the large-diameter steel casing in the shape of a triangle; when steel sheet piles are used as the trench side-wall support, the retaining structure is fabricated and extended to the sheet piles in a shape of =; when the bottom of the outer installation casing for pre-burying the monitoring well is fixed to the bottom of the PRB trench, only one positioning bracket is required, which is installed and fixed, via hoisting or hanging with a steel wire, at a position 2 meters below the top of the monitoring well pipe; otherwise, two positioning brackets are required, and are installed and fixed, via hoisting or hanging with a steel wire, at positions 2 meters below the top of the monitoring well pipe and 2 meters above the bottom of the monitoring well, respectively; the positioning brackets are used to fix and maintain the distances between the outer installation casing for pre-burying the monitoring well and the trench side-wall support, and thereby ensure the vertical installation precision of the monitoring well and prevent adverse impacts on the monitoring well during PRB media backfilling.

In an embodiment, the diameters of the PVC well casings and the well screens in Step 6 range from 50 to 160 millimeters; the monitoring well pipe is made of strong, corrosion-resistant, and pollution-free materials which include, but not limited to, PVC and stainless steel; the length of the monitoring well screen is equal to the backfilled thickness of the PRB reactive media; the sizes of the filter pack material between the monitoring well pipe and the outer installation casing for pre-burying the monitoring well are consistent with the dimension of the well screen apertures or slots; the sand-settling casing has a length of 1 to 2 meters and is mounted at the bottom of the well screen pipe, and the bottom of the monitoring well pipe is sealed with a PVC cap.

In an embodiment, in Step 8, the PRB media are first backfilled in the trench to a depth 0.5 to 1 meter above the groundwater table, and then the covering soil layer is placed on the top of PRB media until it is flush mount with the ground surface.

For the design of specific aperture sizes and percentage of opening area of the monitoring well screen pipe, selection and matching of filter pack materials, and well development methods following well completion, refer to the requirements for well construction in the "Technical Guidelines for the Construction of Groundwater Environmental Monitoring Wells (draft for comments)" issued by the China National Environmental Monitoring Center in 2013, and the "Specifications for the Construction of Groundwater Monitoring Wells" issued by the Ministry of Land and Resources of the People's Republic of China in 2014.

Following the groundwater monitoring well installation method described in this presented invention, PRB trench construction and monitoring well installation inside the trench may be concurrently implemented. Compared to the conventional monitoring well construction and installation method, the presented invention improves the quality of the monitoring well, reduces disturbance and waste of the PRB media, accelerates construction process, and complies with the specifications for well construction issued by national agencies and institutes, thus provides assurances for collection of representative groundwater monitoring samples and evaluation of PRB operation and effectiveness.

The presented invention demonstrates the following advantageous effects:

1. Installation of the groundwater monitoring well and construction of the PRB trench are conducted concurrently, preventing redundant construction work of redrilling inside the PRB trench following its completion.

2. When monitoring wells are installed following the pre-burying method described in the presented invention, which is simple to follow and easy to implement, the construction duration may be shortened (approximately saving one day per monitoring well), and the cost may be reduced.

3. The pre-burying method in the presented invention assures that specifications for monitoring well installation inside PRB trenches and monitoring well quality are achieved and prevents bore hole collapse, blockage, well pipe rupture, etc.

4. The presented invention provides assurance for collection of representative groundwater samples.

5. The presented invention promotes real-time monitoring and evaluation of the quality and lifespan of PRBs, thus provides technical supports for engineering application of the PRB technology at contaminated sites.

Figure 1:
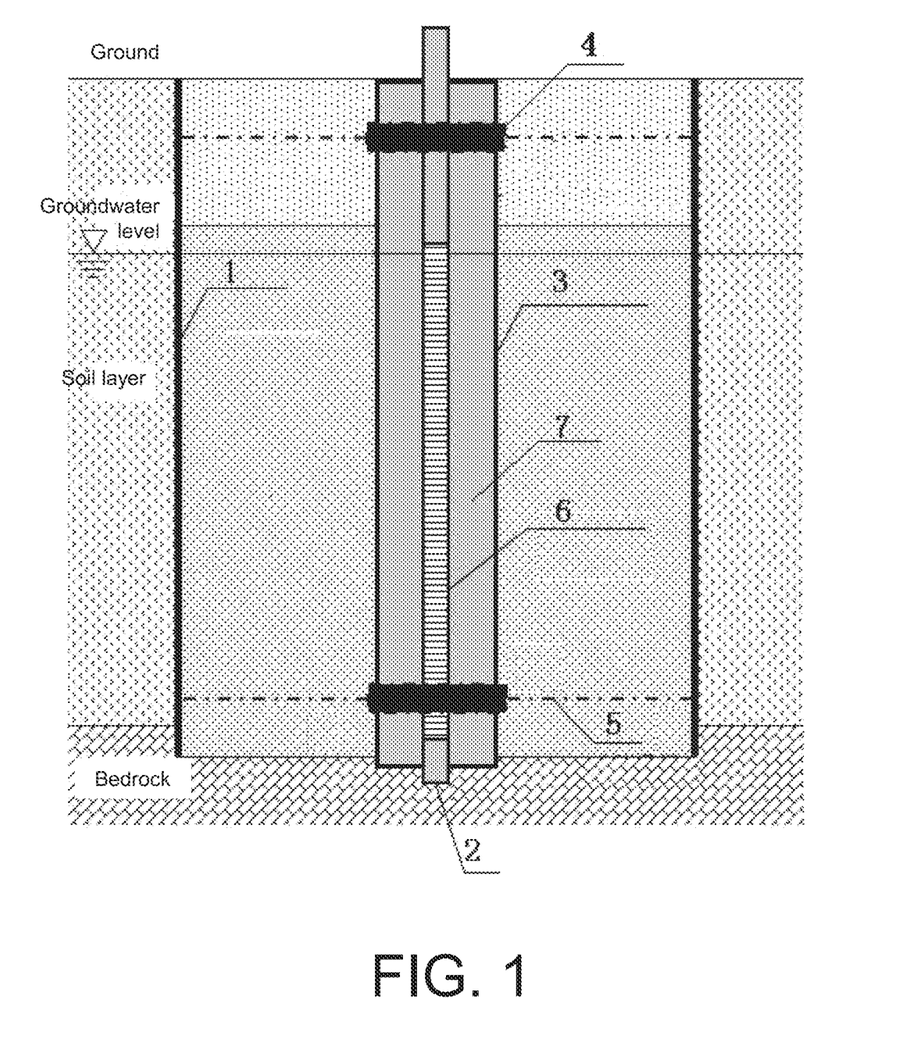
FIG. 1 is a sectional diagram demonstrating the construction of a groundwater monitoring well inside a PRB trench.
Figure 2:
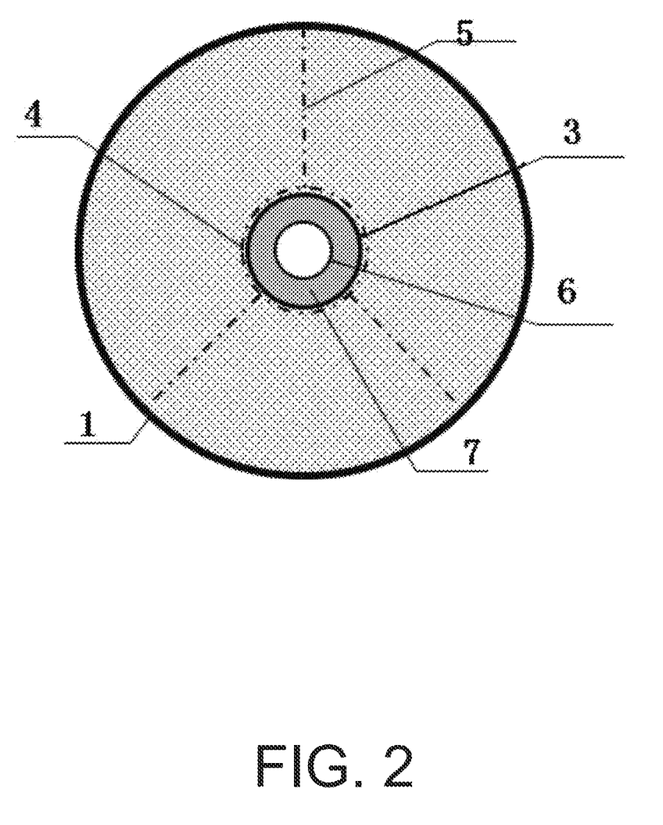
FIG. 2 is a planar diagram demonstrating the installation operation of a groundwater monitoring well inside a PRB trench using a rotary drilling machine.
Figure 3:
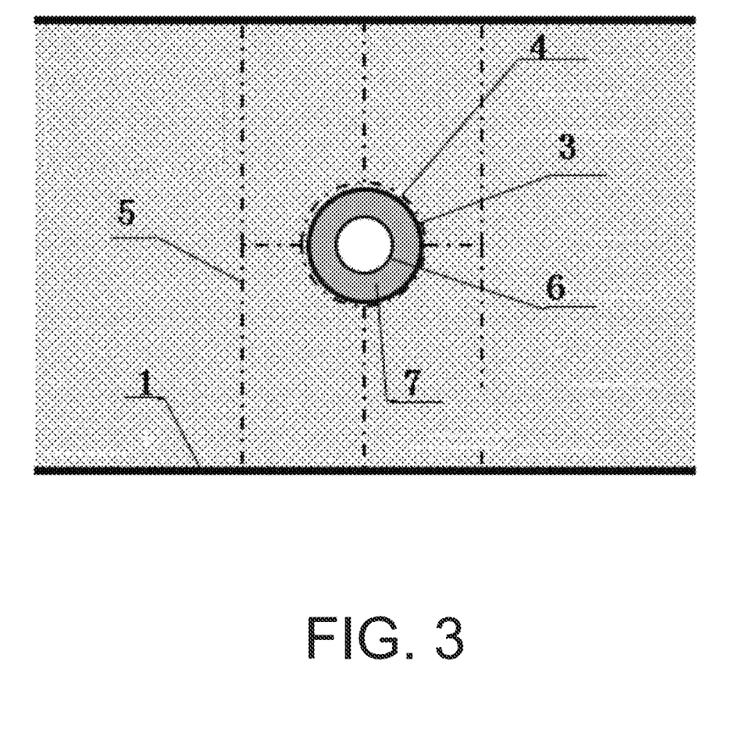
FIG. 3 is a planar diagram demonstrating the installation operation of a groundwater monitoring well inside a PRB trench using a long-reach excavator or a double-wheel milling machine.

Meanings of numerals: (1) trench side-wall support, (2) monitoring well borehole, (3) outer installation casing for pre-burying the monitoring well, (4) hoop, (5) retaining structure, (6) monitoring well pipe, and (7) filter packs and seal materials.

DESCRIPTION OF EMBODIMENTS

The following embodiments are only for the purpose of illustrating the technical ideas and features of the presented invention and aim to help those, who are familiar with the technology, understand the contents of the presented invention and implement accordingly and are not intended to limit the scope of protection for the presented invention. All equivalent modifications and refinement made according to the ideology and theory of the presented invention shall fall within the scope of protection for the presented invention.

Embodiments

In this embodiment, a PRB trench was constructed with a rotary digging and drilling and cast-in-place pile method, and monitoring wells were installed following the method in the presented invention. During well installation, a large-diameter steel casing used for rotary digging and drilling was used as a trench side-wall support which facilitated installation of monitoring wells inside the PRB trench.

The method for installing a groundwater monitoring well inside a PRB trench, as shown in FIGS. 1 and 2, included the following specific steps:

Step 1: Excavating a PRB trench: Excavated with trenching equipment for the construction of a PRB trench, to the design depth, width and length, and clearing soil from the excavated trench. The trenching equipment was a rotary drilling machine. The design depth of the PRB trench was 15 meters, and the design thickness of the PRB trench was 3 meters. The aquiclude layer was heavily weathered bedrock. During construction, a rotary drilling machine initially drilled a pilot borehole to a depth of 1 to 2 meters into the ground, and then a vibratory hammer was used to force the steel casing into the ground till its bottom reached about 12 meters below ground surface. Afterwards, a rotary drilling machine was used to dig to the 15-meter design depth of the PRB trench. Lastly, remaining soil inside the steel casing was removed using a long-reach excavator.

Step 2: Installing a trench side support (1): The large-diameter steel casing served as the trench side-wall support (1), where the diameter, length and thickness of the steel casing for rotary digging and drilling was 1.65 meters, 13 meters, and 0.013 meters, respectively.

Step 3: Positioning a monitoring well borehole: It was determined that the installation location of the groundwater monitoring well inside the PRB trench was at the center of the large-diameter steel casing. A boring machine was used to drill 0.3 to 0.5 meters into the aquiclude layer to form the monitoring well borehole (2) which was used as a positioning and fixing support point for the bottom of the monitoring well pipe. The size of the drill bit was determined by the design diameter of the monitoring well pipe, which was 160 millimeters.

Step 4: Installing an outer installation casing pre-burying the monitoring well (3): The outer installation casing for pre-burying the monitoring well (3) was placed, with a crane or vibratory hammer, at the center of the large-diameter steel casing to the bottom of the excavated PRB trench, wherein the outer installation casing for pre-burying the monitoring well (3) was coaxial with the monitoring well borehole (2). The outer installation casing for pre-burying the monitoring well (3) was made of steel and had a diameter of 36 centimeters, which was 20 centimeters greater than the diameter of the monitoring well, and a length of 15.5 meters, which was 0.5 meters longer than the design depth of the PRB trench. The outer installation casing for pre-burying the monitoring well (3) was forced by the vibratory hammer into the bottom of the PRB trench until the heavily weathered rock was reached, where and the outer installation casing for pre-burying the monitoring well (3) was secured.

Step 5: Installing a monitoring well positioning bracket: The rebar monitoring well positioning bracket included a set of hoop (4) mounted outside the outer installation casing for pre-burying the monitoring well (3) and a retaining structure (5) in attached the hoop (4), wherein the hoop (4) is formed into a ring shape by rolling and pressing a steel bar. The retaining structure (5) was a set of straight rebars with one end welded to the hoop (4) and the other end extended to the trench side-wall support (1) but was not welded, thus ensuring that the outer installation casing for pre-burying the monitoring well (3) was aligned with the trench side-wall support (1). The inner diameter of the hoop (4) was 40 centimeters, which was 4 centimeters larger than the outer diameter of the outer installation casing for pre-burying the monitoring well (3), facilitating mounting, removal, and vertical adjusting movement of the hoop (4). The retaining structure (5) was fabricated with three legs with equal angles, which extended to the large-diameter steel casing in the shape of a triangle. Only one positioning bracket was mounted to secure the outer installation casing for pre-burying the monitoring well (3) and the trench side-wall support (1), maintain the same distance between them, and thereby ensure the vertical installation precision of the monitoring well and prevent adverse impacts on the monitoring well during PRB media backfilling.

Step 6: Installing the monitoring well pipe (6): The monitoring well pipe (6) consisted of a PVC well casing (unslotted pipe), a well screen (slotted pipe), and a sand-settling casing (unslotted pipe) at the bottom, which is assembled with the well casing connected to the top of the well screen and the sand-settling casing connected to the bottom of the well screen. Following the completion of assembly, the assembled monitoring well pipe (6) was lowered into the outer installation casing for pre-burying the monitoring well (3) using a crane, and the bottom of the monitoring well pipe (6) was placed into the fixing support point. A 2-meter sand-settling casing was mounted below the well screen with a PVC cap to seal the end of the monitoring well pipe (6). The diameter of the monitoring well pipe (6) was 160 millimeters. The installed depth intervals of the well casing, the well screen, and the sand-settling casing were 0~7 meters, 7~13 meters, and 13~15 meters below ground surface, respectively.

Step 7: Installing monitoring well filter packs and seal materials (7): The space between the monitoring well pipe (6) and the outer installation casing for pre-burying the monitoring well (3) was filled with the filter packs. Then the space was filled with buffering sands on the top of the filter packs to a thickness of 0.5 to 1 meter. Lastly, the space was filled with bentonite from the top of buffering sands to ground surface to seal the outer installation casing for pre-burying the monitoring well (3).

Step 8: Backfilling the trench with PRB media and capping with a covering soil layer: The trench between the trench side-wall support (1) and the outer installation casing for pre-burying the monitoring well (3) was backfilled with PRB media, in layers of a thickness of 2 meters. The PRB media were first backfilled in the trench to a depth 0.5 to 1 meter above the groundwater table, and then a covering soil layer was placed on the top of PRB media until it was flush mount with the ground surface.

Step 9: Removing the outer installation casing for pre-burying the monitoring well (3): Backfilling was suspended every time the thickness of backfilled media reached 2 meters, the outer installation casing for pre-burying the monitoring well (3) was then pulled up with a crane or vibratory hammer by 2 meters, and backfilling resumed afterwards. This alternated operations of backfilling PRB media and pulling up the outer installation casing for pre-burying the monitoring well (3) was implemented until the PRB trench was completely backfilled and the outer installation casing for pre-burying the monitoring well (3) was completely pulled out of the ground. In this way, installation of the monitoring well and backfilling the PRB trench were completed concurrently.

Step 10: Removing the trench side-wall support (1): The trench side-wall support (1) (large-diameter steel) casing was removed with a vibratory hammer or a hoisting device following the removal of the outer installation casing for pre-burying the monitoring well (3).

Step 11: Conducting well completion and well development: Lastly, a well head assembly and a well cap were installed for the groundwater monitoring well installed inside the PRB trench. The elevation of the top of casing was surveyed. Well development for the installed groundwater monitoring well was conducted to complete preparation for groundwater sampling.

Figure 4:
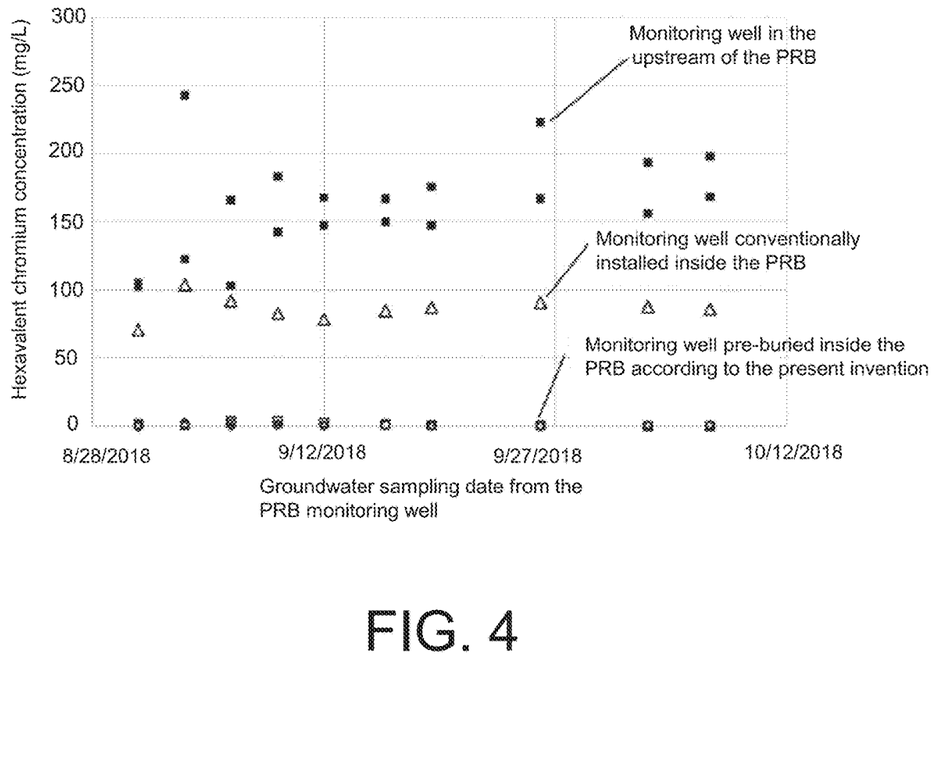
FIG. 4 is a diagram demonstrating comparison of sampling data collected from groundwater monitoring wells inside a PRB trench, which were installed with different methods.

FIG. 4 demonstrates a comparison between the hexavalent chromium concentration data obtained by analyzing samples collected from groundwater monitoring wells inside a PRB trench that were installed in different methods in this embodiment. In FIG. 4, the data corresponding to a "monitoring well pre-buried inside the PRB according to the present application" were obtained from groundwater samples collected from a monitoring well pre-buried in the PRB trench during PRB construction in this presented application; the data corresponding to a "monitoring well conventionally installed inside the PRB" were obtained from groundwater samples collected from a monitoring well installed by re-drilling inside the PRB trench after PRB construction was completed; and the data corresponding to a "monitoring well in the upstream of the PRB" were collected from groundwater samples collected from a monitoring well installed outside the PRB trench and upstream of the groundwater flow field and were used for comparison and reference. As shown in FIG. 4, the data obtained from groundwater samples collected from a monitoring well pre-buried in the PRB trench during PRB construction were highly consistent and representative, reflecting the actual result of the treatment of hexavalent chromium contaminated groundwater with the PRB media. On the other hand, well installed by re-drilling in the PRB trench after construction completion likely imposed an adverse impact on the hydraulic connection between the PRB media and the surrounding groundwater aquifer, and the data collected from this monitoring well did not reflect the actual result of the treatment of hexavalent chromium contaminated groundwater with the PRB media. The data in this embodiment suggest that groundwater data that are more representative and reliable may be obtained from monitoring wells pre-buried in the PRB trench during PRB construction following the method in this presented application, thus provide technical support for the real-time monitoring and evaluation of the quality and lifespan of a PRB and the engineering application of the PRB technology in contaminated sites.

What is claimed is:

1. A method for installing a groundwater monitoring well inside a PRB trench, specifically comprising following steps:
   Step 1: excavating a PRB trench: excavating with trenching equipment for construction of the PRB trench, to a design depth, width, and length, and cleaning soil from the excavated trench;
   Step 2: installing a trench side-wall support: when a rotary drilling machine is used to excavate the PRB trench, a large-diameter steel casing serves as the trench side-wall support, wherein the large-diameter steel casing has a diameter larger than 1 meter; when a long-reach excavator or a double-wheel milling machine is used to excavate the PRB trench, steel sheet piles serve as the trench side-wall support;
   Step 3: positioning a monitoring well borehole: determining an installation location of the groundwater monitoring well inside the PRB trench at a center of the large-diameter steel casing or at a mid-point between the steel sheet piles on both sides of the PRB trench, and drilling 0.3 to 0.5 meters into an aquiclude layer with a drilling machine to form the monitoring well borehole, and using the monitoring well borehole as a positioning and fixing support point for a bottom of a monitoring well pipe;
   Step 4: installing an outer installation casing for pre-burying the groundwater monitoring well: Placing, with a crane or vibratory hammer, the outer installation casing for the groundwater monitoring well at the bottom of the excavated PRB trench, wherein the outer installation casing is coaxial with the monitoring well borehole;
   Step 5: installing a monitoring well positioning bracket: the monitoring well positioning bracket including a hoop mounted outside the outer installation casing for the groundwater monitoring well and a retaining structure attached to the hoop, wherein the hoop is formed into a ring shape by rolling and pressing a steel bar; the retaining structure is a set of straight rebars with one end welded to the hoop and the other end in contact with the trench side-wall support;
   Step 6: installing the monitoring well pipe: the monitoring well pipe consists of a PVC well casing, a well screen, and a sand-settling casing, the well casing, the well screen, and the sand-settling casing being assembled to form the monitoring well pipe in a manner of the well casing connected to a top of the well screen and the sand-settling casing connected to a bottom of the well screen; following completion of assembly, lowering the monitoring well pipe into the outer installation casing for the groundwater monitoring well using a crane and placing the bottom of the monitoring well pipe into the fixing support point that is formed by previously drilling at the bottom of the monitoring well pipe;
   Step 7: installing monitoring well filter packs and seal materials: filling a space between the monitoring well pipe and the outer installation casing for the groundwater monitoring well with the filter packs; then filling the space with buffering sands on a top of the filter packs to a thickness of 0.5 to 1 meter; and then filling the space with bentonite from a top of the buffering sands to a ground surface to seal the outer installation casing for the groundwater monitoring well;
   Step 8: backfilling the PRB trench with PRB trench backfill materials: backfilling the PRB trench with the PRB trench backfill materials between the trench side-wall support and the outer installation casing for pre-burying the groundwater monitoring well, in layers of a thickness of 2 meters, wherein the PRB trench backfill materials include a trench media and a covering soil layer;
   Step 9: removing the outer installation casing for pre-burying the groundwater monitoring well: suspending the backfilling of the backfill material every time the thickness of the backfill material reaches 2 meters, pulling up the outer installation casing for pre-burying the groundwater monitoring well with a crane or a vibratory hammer by 2 meters, and resuming the backfilling afterwards; repeating the alternated operations of backfilling of the backfill material and pulling up the outer installation casing for pre-burying the groundwater monitoring well until the trench is completely backfilled and the outer installation casing for pre-burying the groundwater monitoring well is completely pulled out of the ground; wherein, in this way, installation of the groundwater monitoring well and backfilling the PRB trench are completed concurrently;
   Step 10: removing the trench side-wall support: following removal of the outer installation casing for pre-burying the groundwater monitoring well, removing the trench side-wall support with a vibratory hammer or a hoisting device; and,
   Step 11: conducting well completion and well development: lastly, installing a well head assembly for the groundwater monitoring well installed inside the PRB trench, and conducting the well development for the installed groundwater monitoring well to complete preparation for groundwater sampling.

2. The method for installing the groundwater monitoring well inside the PRB trench according to claim 1, wherein a design depth of the PRB trench in Step 1 is 0.5 to 1 meter from a bottom of the PRB trench into the aquiclude layer; the aquiclude layer is a bedrock or a clay layer; the design width of the PRB trench is 1 to 3 meters; and the trenching equipment is a rotary drilling machine, a turntable drilling machine, a long-reach excavator or a double-wheel milling machine.

3. The method for installing the groundwater monitoring well inside the PRB trench according to claim 1, wherein the steel sheet piles are to be installed as forced into a ground by vibration of a vibratory hammer on the both sides of the PRB trench.

4. The method for installing the groundwater monitoring well inside the PRB trench according to claim 1, wherein a size of a drill bit of the drilling machine in Step 3 is determined by a design diameter of the monitoring well pipe, and the diameter of the monitoring well pipe ranges from 50 millimeters to 160 millimeters.

5. The method for installing the groundwater monitoring well inside the PRB trench according to claim 1, wherein a material of the outer installation casing for pre-burying the groundwater monitoring well in Step 4 is steel, and a diameter of the groundwater monitoring well is larger than or equal to 110 millimeters; an inner diameter of the outer installation casing for pre-burying the groundwater monitoring well is larger than an outer diameter of the monitoring well pipe by at least 10 centimeters, and a length of the outer installation casing for pre-burying the groundwater monitoring well is 0.3 to 0.5 meters longer than the design depth of the PRB trench.

6. The method for installing the groundwater monitoring well inside the PRB trench according to claim 1, wherein a material of the monitoring well positioning bracket in Step 5 is steel, and the hoop has an inner diameter of 2 to 4 millimeters greater than an outer diameter of the outer installation casing for pre-burying the groundwater monitoring well; the retaining structure is made of rebar; when the large-diameter steel casing is used as the trench side-wall support, the retaining structure is fixed to the large-diameter steel casing in a shape of a triangle; when the steel sheet piles are used as the trench side-wall support, the retaining structure is fixed to the steel sheet piles in a shape of I; when a bottom of the outer installation casing for pre-burying the groundwater monitoring well is fixed to the bottom of the PRB trench, only one positioning bracket is required, which is installed and fixed, via hoisting or hanging with a steel wire, at a position 2 meters below a top of the monitoring well pipe; otherwise, two positioning brackets are required, and are installed and fixed, via hoisting or hanging with a steel wire, at positions 2 meters below the top of the monitoring well pipe and 2 meters above a bottom of the groundwater monitoring well, respectively; the positioning brackets are used to fix and maintain a distance between the outer installation casing for pre-burying the groundwater monitoring well and the trench side-wall support, and thereby ensuring a vertical installation precision of the groundwater monitoring well and preventing adverse impacts on the groundwater monitoring well during backfilling the PRB trench.

7. The method for installing the groundwater monitoring well inside the PRB trench according to claim 1, wherein the diameters of the PVC well casing and the well screen in Step 6 range from 50 to 160 millimeters; the monitoring well pipe is made of corrosion-resistant, and pollution-free materials which include, PVC pipe and stainless steel pipe; a length of a monitoring well screen is equal to a backfilled thickness of a PRB reactive media; sizes of materials of the filter packs between the monitoring well pipe and the outer installation casing for pre-burying the groundwater monitoring well are consistent with dimensions of apertures or slots of the well screen; the sand-settling casing has a length of 1 to 2 meters and is mounted at the bottom of the well screen pipe, and the bottom of the monitoring well pipe is sealed with a PVC cap.

8. The method for installing the groundwater monitoring well inside the PRB trench according to claim 1, wherein in Step 8, the trench media are first backfilled in the PRB trench to a depth 0.5 to 1 meter above a groundwater table, and then the covering soil layer is placed on a top of trench media until it is flush mount with the ground surface.

\* \* \* \* \*

UNITED STATES PATENT AND TRADEMARK OFFICE
CERTIFICATE OF CORRECTION

| | |
|---|---|
| PATENT NO. | : 11,454,114 B2 |
| APPLICATION NO. | : 17/568726 |
| DATED | : September 27, 2022 |
| INVENTOR(S) | : Xin Song et al. |

It is certified that error appears in the above-identified patent and that said Letters Patent is hereby corrected as shown below:

On the Title Page

Column 1, Item (71) Applicant should read: INSTITUTE OF SOIL SCIENCE, CHINESE ACADEMY OF SCIENCES, Jiangsu (CN)

Signed and Sealed this
Thirteenth Day of December, 2022

*Katherine Kelly Vidal*

Katherine Kelly Vidal
*Director of the United States Patent and Trademark Office*